United States Patent
Fujii et al.

(10) Patent No.: US 6,829,047 B2
(45) Date of Patent: Dec. 7, 2004

(54) DEFECT DETECTION SYSTEM

(75) Inventors: Tatsuya Fujii, Tokyo (JP); Ayumu Onoyama, Tokyo (JP); Koichi Sakurai, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 313 days.

(21) Appl. No.: 10/061,235

(22) Filed: Feb. 4, 2002

(65) Prior Publication Data

US 2002/0149765 A1 Oct. 17, 2002

(30) Foreign Application Priority Data

Apr. 13, 2001 (JP) ........................................ 2001-115288

(51) Int. Cl.⁷ .............................................. G01N 21/00
(52) U.S. Cl. ................................. 356/237.4; 356/237.5; 356/394; 250/559.36
(58) Field of Search ........................... 356/237.1, 237.2, 356/237.3, 237.4, 237.5, 394; 250/559.36, 559.22, 149, 190, 126.129

(56) References Cited

U.S. PATENT DOCUMENTS

| | | | | |
|---|---|---|---|---|
| 4,112,309 A | * | 9/1978 | Nakazawa et al. | 250/559.24 |
| 4,559,603 A | * | 12/1985 | Yoshikawa | 716/5 |
| 4,639,604 A | * | 1/1987 | Murakami et al. | 250/548 |
| 4,845,558 A | * | 7/1989 | Tsai et al. | 348/126 |
| 5,153,444 A | * | 10/1992 | Maeda et al. | 250/559.05 |
| 5,574,800 A | * | 11/1996 | Inoue et al. | 382/149 |
| 5,649,022 A | * | 7/1997 | Maeda et al. | 382/141 |
| 5,982,922 A | * | 11/1999 | Moriya | 382/149 |

FOREIGN PATENT DOCUMENTS

| | | |
|---|---|---|
| JP | 61271831 | 12/1986 |
| JP | 5281154 | 10/1993 |
| JP | 7147309 | 6/1995 |
| JP | 11251386 | 9/1999 |

* cited by examiner

*Primary Examiner*—Hoa Q. Pham
(74) *Attorney, Agent, or Firm*—Burns, Doane, Swecker & Mathis, L.L.P.

(57) ABSTRACT

A defect detection system to check any defect in the pattern to be checked by comparing a pattern to be checked with a reference pattern includes an edge detection means for detecting a pattern edge of the pattern to be checked by scanning a substrate by laser beams and detecting reflected light thereof. After the relative position between the substrate and the imaging means is adjusted so that the pattern edge of the pattern to be checked is substantially aligned with one side of CCD pixels, an image of the pattern to be checked is picked up. Therefore, the defect detection system corrects misalignment less than one pixel between a pattern to be checked and a reference pattern to prevent occurrence of a false defect.

10 Claims, 7 Drawing Sheets

DEFECT DETECTION SYSTEM

BACKGROUND OF THE INVENTION

The present invention relates to a defect detection system and more particularly to a defect detection system for detecting defects in minute patterns.

A defect detection system for checking any defect in wiring patterns or the like on a semiconductor substrate compares a reference pattern free from any defect with a pattern to be checked to detect a point with different pattern shapes as a defect.

FIGS. 7A and 7B show an example of a defect detection process described in JP, 5-281154, A. FIG. 7A is a top view of a pattern to be checked or a reference pattern 50. The central rectangular region in a form of 4×4 matrix is a region to be checked 51. The regions along the four sides are alignment regions 52.

In such a checking process, an edge detection filter 53 composed of successive four CCD pixels shown in FIG. 7B is used. For example, a case where an edge to be detected extends vertically is considered. The edge detection filter 53 is overlaid on the alignment region 52 above the region to be checked 51. Then, gray levels of four pixels ($f_{i,j}$, $f_{i+1,j}$, $f_{i+2,j}$, $f_{i+3,j}$) of the edge detection filter 53 are detected. The filter output of the four pixels is shown by the following equation:

$$f_{i,j} - f_{i+1,j} - f_{i+2,j} + f_{i+3,j}$$

As shown in FIG. 7B, the following detection results are obtained: (1) when the filter output is negative (−), the edge is between $f_{i,j}$ and $f_{i+1,j}$; (2) when the filter output is 0, the edge is between $f_{i+1,j}$ and $f_{i+2,j}$; and (3) when the filter output is positive (+), the edge is between $f_{i+2,j}$ and $f_{i+3,j}$. In this manner, the edge detection is performed to both of the pattern to be checked and the reference pattern at the four peripheral sides of the region to be checked 51.

Next, each difference of the edge positions at the four sides between the pattern to be checked and the reference pattern is obtained. Then, the relative position of the pattern to be checked and the reference pattern is corrected so that the sum of the absolute values of such differences is minimal.

At last, the pattern to be checked and the reference pattern are compared with each other and, if there is any difference therebetween, it is determined that the checked pattern has a defect.

In such a defect detection process, the relative position between the pattern to be checked and the reference pattern is corrected in one pixel of the edge detection filter 53 (one pixel of the CCD). Therefore, misalignment less than one pixel cannot be corrected. When a wiring layer accounts for 60% of one pixel of the edge detection filter 53, for example, such misalignment cannot be detected because the wiring layer is considered to occupy whole one pixel.

However, with recent micro miniaturization of semiconductor devices, the pattern width of a wiring layer, etc. becomes equal to or smaller than the width of one CCD pixel. Thus the size of a defect to be detected by a defect detection system is less than one pixel. When there is misalignment less than one pixel between a pattern to be checked and a reference pattern, it is detected as a defect in the pattern although it is not an actual defect, resulting in a problem of a false defect.

SUMMARY OF THE INVENTION

Therefore, it is an object of the present invention to provide a defect detection system to correct a misalignment less than one pixel between a pattern to be checked and a reference pattern and prevent occurrence of a false defect.

The present invention provides a defect detection system for checking any defect in a pattern to be checked by comparing the pattern with a reference pattern, including: a stage for carrying a substrate on which a pattern to be check is formed; an edge detection means for detecting a pattern edge of the pattern to be checked by scanning laser beams on the substrate and detecting reflected light thereof; an imaging means positioned above the stage and for picking up an image of the pattern to be checked using a charge coupled device (CCD); a detection means for checking for any defect in the pattern to be checked by comparing data of the pattern to be checked obtained by the imaging means with data of the reference pattern; and an adjustment means for adjusting the relative position of the substrate and the imaging means, in which the imaging means picks up an image of the pattern to be checked after the adjustment means adjusts the relative position of the substrate and the imaging means so that the pattern edge of the pattern to be checked is aligned with a side of pixels of the CCD.

With such a defect detection system, a pattern edge is detected using laser beams and the pattern edge is aligned with the edge of the pixels. This can prevent occurrence of a fault defect resulting from the misalignment of the pattern edge and the edge of the pixels and thus perform precise checking of the pattern.

Especially, high-precision defect detection can be performed even for a pattern with a width smaller than that of one pixel of the imaging camera. For this reason, high-precision defect detection of micro-miniaturized and integrated semiconductor devices can be performed easily.

Preferably, the edge detection means includes a light source of said laser beams and a detector for receiving reflected light of the laser beams.

The use of such laser beams allows accurate detection of the pattern edge of the pattern to be checked.

Preferably, the edge detection means is a means for detecting said pattern edge by radiating the substrate with two independent laser beams from two different directions.

Preferably, the horizontal components (components substantially parallel to the surface of the substrate) of the two laser beams are substantially orthogonal to each other.

Preferably, the edge detection means is a means for detecting a position radiated with the laser beams at peak scattering light intensity of the reflected light as the pattern edge of the pattern to be checked.

Preferably, the incident angle of the laser beams is approx. 45° with respect to the substrate on which a pattern to be checked is formed.

The edge detection means may include a polarizer selected between a linear polarizer and phase shifter, polarizes the laser beams and radiates them on the substrate.

The use of polarized laser beams for detection of the pattern edge facilitates the detection of change in scattering intensity in the pattern edge and allows accurate detection of the pattern edge.

Preferably, the adjustment means is a means for adjusting the relative position of the stage and the imaging means by moving at least one of the stage and the imaging means.

In other words, considering the configuration and structure of the defect detection system, it is preferable that the stage and/or imaging means should be moved so that the pattern edge of the pattern to be checked on the stage should be aligned with the edge of the pixels of the imaging means.

The data of the reference pattern may be the data of the non-defective pattern selected from a plurality of the patterns to be checked. Based on the image data of the pattern to be checked, the defects of other patterns to be checked are checked.

The data of the reference pattern may be CAD data of the pattern to be checked. Based on such CAD data, the defects of the pattern to be checked are checked.

The pattern width of the pattern to be checked may be smaller than the width of the pixels.

With a defect detection system in accordance with the present invention, a pattern edge is detected using laser beams and the pattern edge can be aligned with the edge of the pixels even for a pattern to be checked with a pattern width smaller than that of CCD pixels in the imaging means. This allows high-precision defect detection even for such a pattern to be checked with a smaller pattern width.

As described above, the use of the defect detection system in accordance with the present invention can prevent the detection of misalignment between the pattern edge and the edge of the pixels as a false defect.

This allows high-precision defect detection of a pattern having a width smaller than that of one pixel of an imaging camera.

DETAILED DESCRIPTION OF THE PREFERRED EMBODIMENTS

Figure 1:
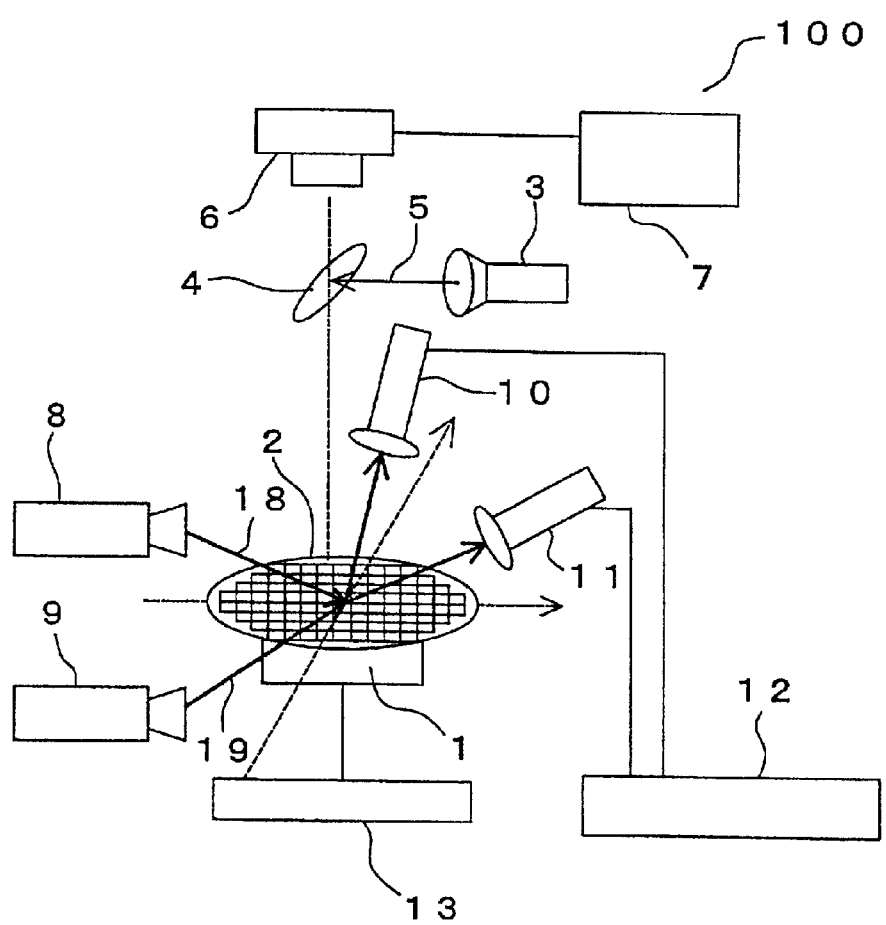
FIG. 1 is a schematic view of a defect detection system in accordance with the present invention.

FIG. 1 is a schematic view of a defect detection system in accordance with the present invention, generally indicated at reference numeral 100. The defect detection system 100 includes a stage 1. The stage 1 has reference axes composed of two orthogonal axes (X- and Y- axes). The laser radiation position and imaging camera position, which will be described below, are established with respect to these reference axes. The stage 1 can move in the directions of the X-axis and Y-axis, and in a rotation direction of θ on the X-Y plane. The stage 1 carries a wafer 2 to be checked thereon.

The defect detection system 100 also includes a light source 3 and a half mirror 4 positioned above the stage 1. Light 5 emitted from the light source 3 is reflected by the half mirror 4 and radiated onto the wafer 2 to be checked. In addition, an imaging camera 6 with a CCD is provided above the stage 1. The imaging camera 6 picks up an image of the pattern on the wafer 2 to be checked through the half mirror 4. The image data obtained is transmitted to an image processing/image comparing unit 7.

The defect detection system 100 further includes laser units X 8 and Y 9. Laser beam 18 emitted from the laser unit X 8 is directed onto the surface of the wafer 2 to be checked from a diagonally upward direction with regard to the X-axis on the stage 1. The laser beam 18 reflected by the surface of the wafer 2 to be checked is directed toward a light receiving unit X 11 and is detected. Similarly, laser beam 19 emitted from the laser unit Y 9 is directed onto the surface of the wafer 2 to be checked from a diagonally upward direction with regard to the Y-axis on the stage 1. The laser beam 19 reflected by the surface of the wafer 2 to be checked is directed toward a light receiving unit Y 10 and is detected. Preferably, the incident angles of the laser beams 18 and 19 are approx. 45° with respect to the surface of the wafer 2 to be checked.

The data detected by the light receiving units X 11 and Y 10 is transmitted to a pattern edge position detection unit 12 composed of a computer or the like.

The pattern edge position detection unit 12 detects, as the pattern edge of the pattern on the wafer 2 to be checked, the position with the peak scattering intensity, based on the scattering intensity of laser beams 18 and 19 detected at light receiving units X 11 and Y 10. Such position information of the pattern edge is stored on X-Y coordinates of the reference axes.

Figure 2A:
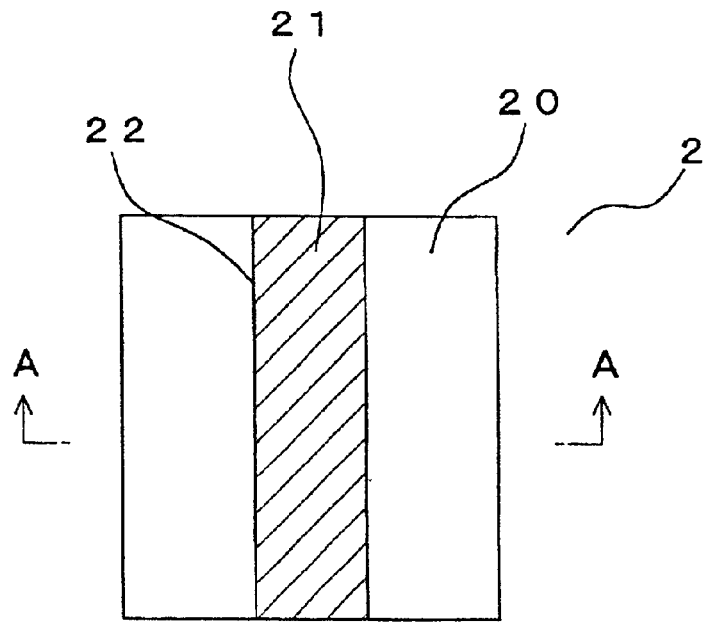
FIG. 2 shows an example of a process of detecting a pattern edge.
Figure 2B:
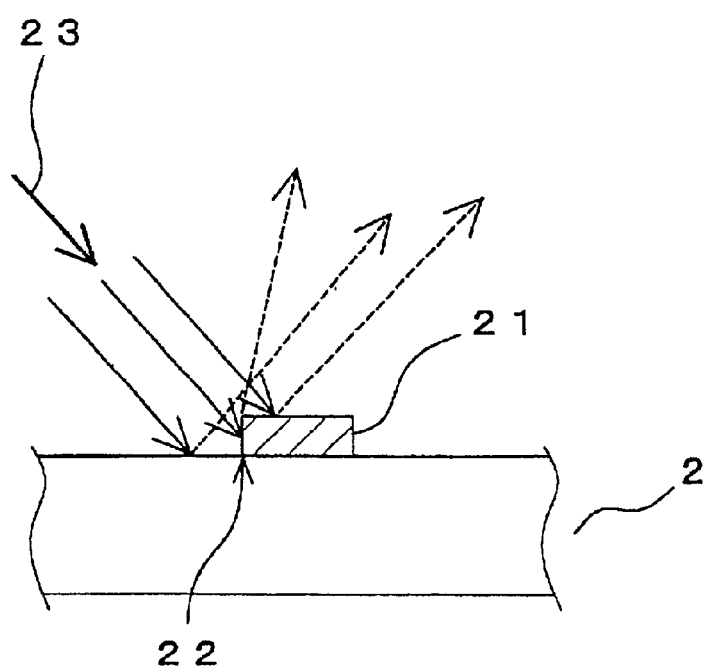

FIGS. 2A and 2B show a part of a pattern edge detection process. FIG. 2A shows a part of the wafer 2 to be checked having a metallic pattern 21, for example, formed on substrate 20. FIG. 2B is a cross section taken along the line A—A of FIG. 2A.

As shown in FIG. 2B, laser beam 23 for detecting a pattern edge 22 is directed onto the surface of the substrate 20 at an incident angle of approx. 45° and the laser beam reflected by the surface is detected by a detector (not shown). As the stage (not shown) carrying the substrate 20 moves, the laser beam 23 scans the substrate 20. In FIG. 2B, scanning is performed in the direction of the left to right. When the scanned laser beam 23 impinges upon the sidewall of the pattern 21, it is scattered and the intensity of the reflected light received by the detector (not shown) decreases. Therefore, the detection of the position with the peak scattering intensity of the laser beam 23 can determine the pattern edge 22. The intensity distribution of the reflected light detected by the detector is transmitted to a pattern edge position detection unit (not shown) and stored as position information (coordinate data) on the reference axes.

In addition, the laser beam 23 can scan the whole surface of the wafer 2 to be checked by moving the stage in the direction of the Y-axis of reference axes at regular intervals while reciprocating the stage along the X-axis.

Figure 3:
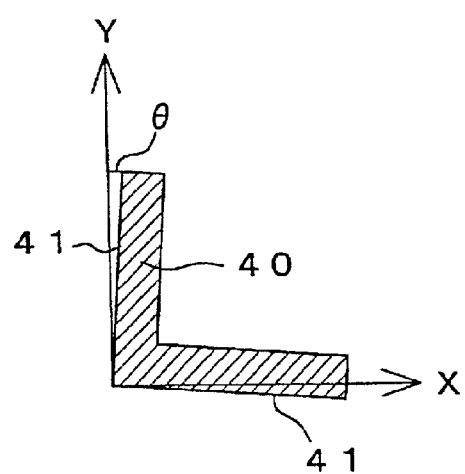
FIG. 3 shows an example of a detected pattern.

FIG. 3 shows an example of a pattern 40 with pattern edges 41 detected in this manner. As seen from FIG. 3, the pattern edges 41 of the pattern 40 are inclined with respect to the X-axis and Y-axis of the reference axes by an angle of θ.

In such a case, the pattern edge position detection unit 12 shown in FIG. 1 gives a signal to a stage control circuit 13. The stage 1 is rotated by an angle of θ and the pattern edges 41 are corrected so as to be placed in the same directions as those of the X-axis and Y-axis. After the correction is made so that pattern edges 41 are parallel to the X-axis and Y-axis, the laser beam 23 scans again so that the position information of the pattern edges 41 is obtained.

On the other hand, the position information (coordinates) of the edge of CCD pixels of the imaging camera 6 is stored in the stage control circuit 13 in advance. Using this information, the stage 1 is moved so that the distance between the edge of the pixels and the pattern edges 41 is substantially zero.

FIGS. 4A to 4D show examples of the cases where the pattern edge and the edge of CCD pixels are brought into alignment. In the drawings, reference numerals 30 and 31, respectively, indicate a substrate and CCD pixels 31 being shown so that they overlie the substrate. A reference numeral 32 indicates a pattern formed on the substrate 30 and 33 indicates a pattern edge thereof. In FIGS. 4A to 4D, misalignment in the direction of θ has already been corrected.

Figure 4A:
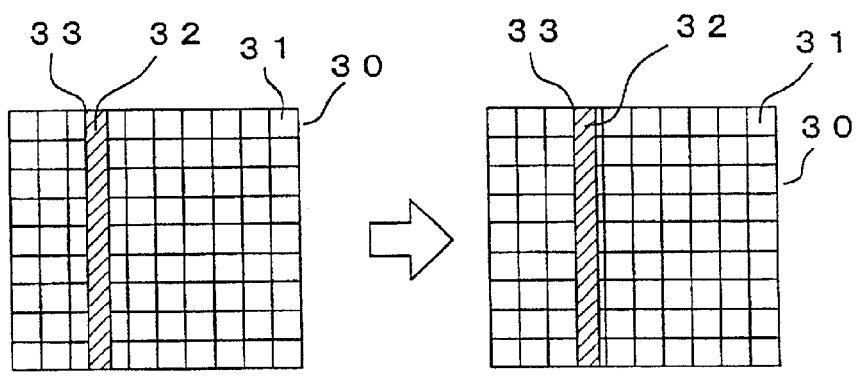
FIG. 4 shows an example of a process of aligning a pattern edge with an edge of CCD pixels.
Figure 4B:
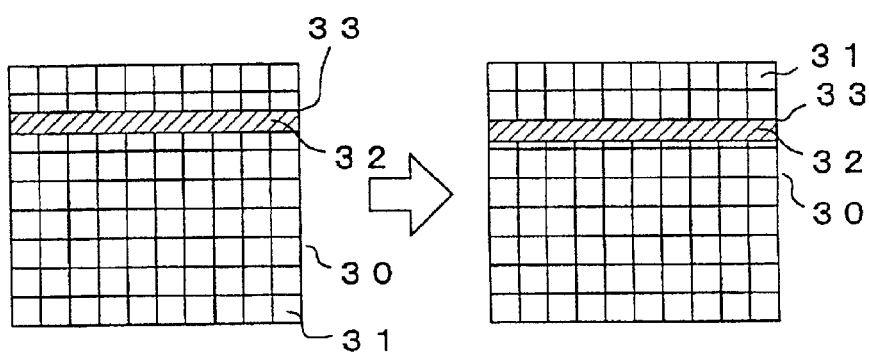
Figure 4C:
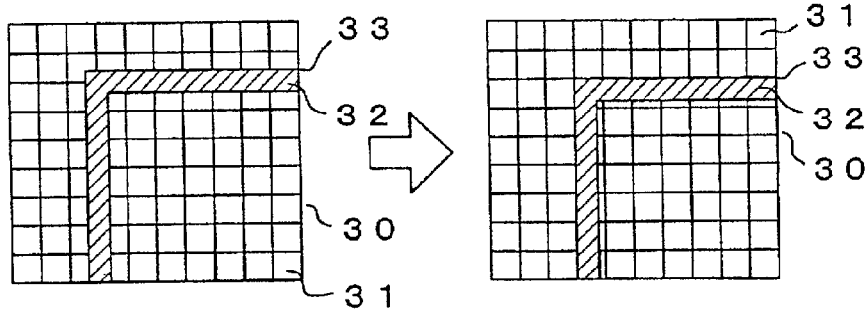
Figure 4D:
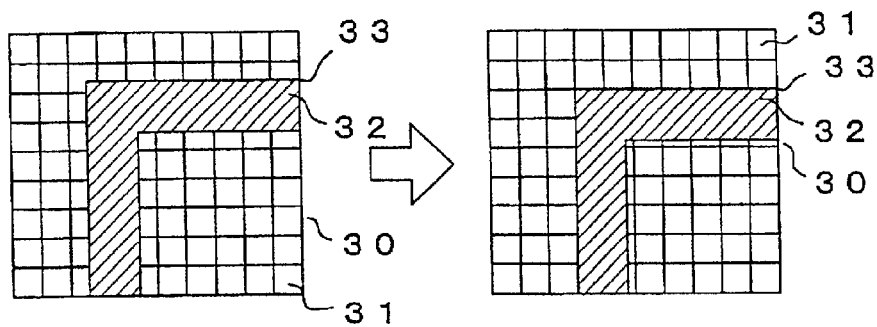

In FIG. 4A, the pattern edge 33 at the left side of the pattern 32 is aligned with the edge of the pixels. In FIG. 4B, the pattern edge 33 at the upper side of the pattern 32 is aligned with the edge of the pixels. In addition, in FIG. 4C, the pattern edge 33 at the left side and upper side of the pattern 32 is aligned with the edges of the pixels. While the width of the pattern 32 is smaller than that of one pixel in FIGS. 4A to 4C, the width of the pattern is larger than that of one pixel in FIG. 4D. Also in the case of FIG. 4D, the pattern edge 33 at the left side and upper side of the pattern 32 is aligned with the edges of pixels.

After such alignment between the pattern edge and the edge of the pixels has been performed, an image of the pattern to be checked is picked up by the imaging camera 6 to obtain image data. The obtained image data is stored in the image processing/image comparing unit 7 composed of a computer or the like.

In the image processing/image comparing unit 7, image data of a reference pattern free from any defect is stored. Such image data of the reference pattern may be CAD data of a pattern to be checked or data obtained by picking up an image of a non-defective pattern to be checked.

Then, the pattern to be checked and the reference pattern are compared in the image processing/image comparing unit 7 and the different part between the patterns is detected as a defect.

Figure 5:
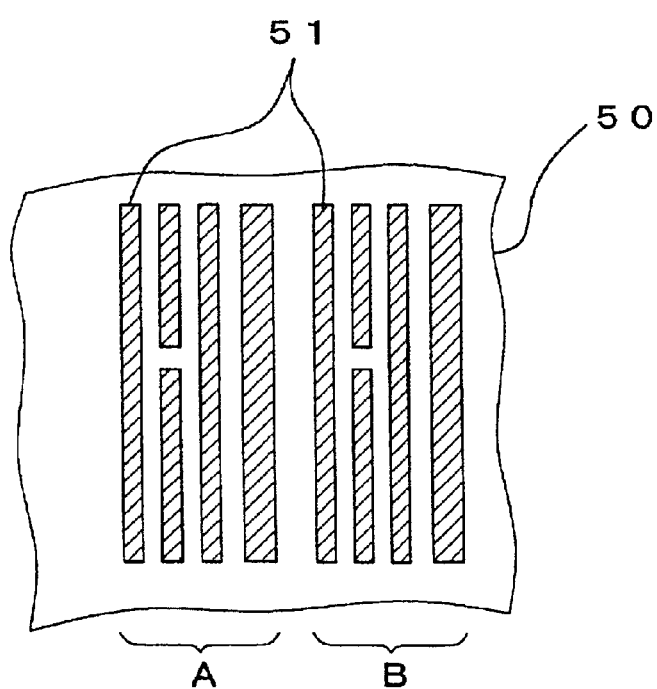
FIG. 5 shows a cell array repeatedly formed on one die.

There are two kinds of methods for such image comparison check. One is a die-to-die comparison check, in which each pattern to be checked on a plurality of dies on the wafer 2 to be checked is compared with a reference pattern. The other is a cell-to-cell comparison check, in which a pattern of cells to be checked in each die is compared with a reference pattern. In other words, a pattern of cell arrays 51 repeatedly formed on one die 50 is compared with a reference pattern (see A and B in FIG. 5).

In accordance with the present invention, the pattern edge of a pattern to be checked and the edge of pixels can be brought into alignment for each die in the same manner, in the die-to-die comparison check. This can prevent occurrence of a false defect resulting from misalignment less than one pixel between the pattern edge and the edge of pixels.

In the cell-to-cell comparison check, the position relationship between respective cell pattern and edge of pixels is equal for each cell. This allows defect detection on the entire wafer surface at maximum sensitivity.

In the defect detection system 100, the laser units X 8 and Y 9 are provided so that the horizontal components of the laser beams 18 and 19 are substantially orthogonal to each other. However, they are not necessarily orthogonal. In other words, the angle between the laser beams 18 and 19 need not be 90° as long as the pattern edge of the pattern on the wafer 2 to be checked can be detected as shown in FIG. 2B. In some patterns, the pattern edges can be detected with either of the laser beam 18 or 19 only.

The laser beams 18 and 19 used in the defect detection system 100 may be polarized using a linear polarizer (not shown). When such a polarizer is used, change in scattering light intensity necessary for the detection of the pattern edge can efficiently be detected. The laser beams 18 and 19 may be elliptically polarized or circularly polarized using a phase shifter (not shown), which allows the efficient detection of change in scattering light intensity necessary for the detection of the pattern edge.

Figure 6:
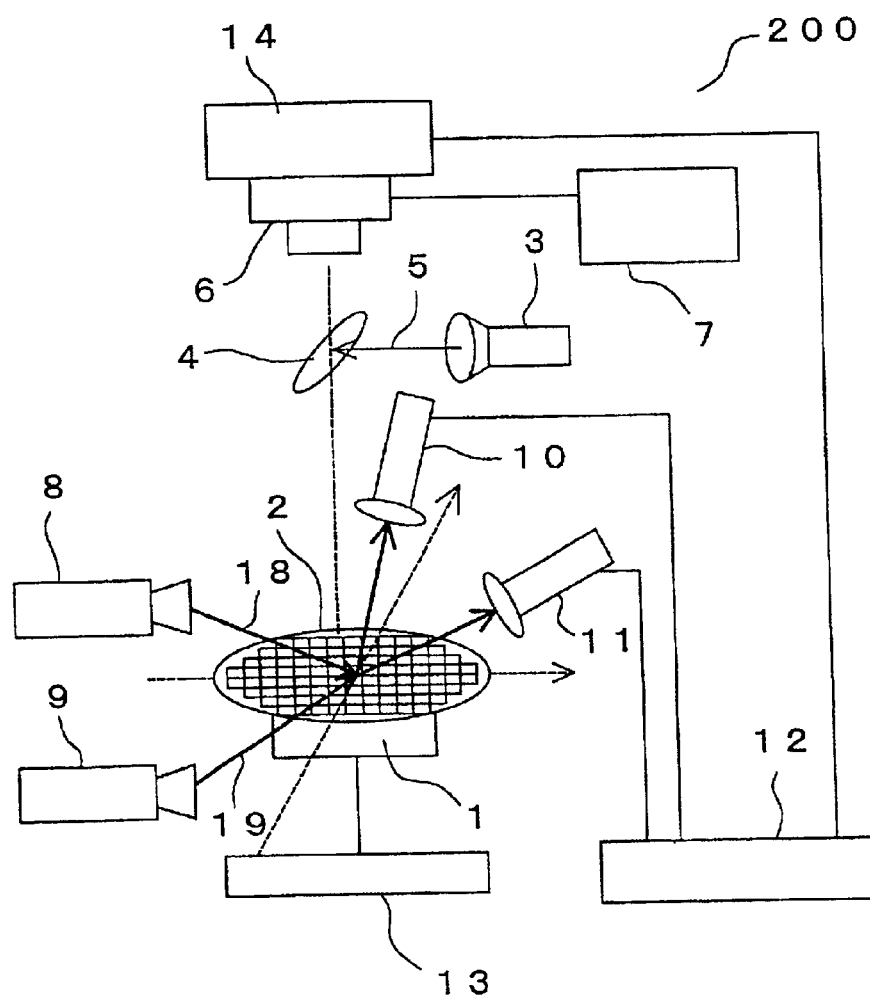
FIG. 6 is a schematic view of another defect detection system in accordance with the present invention.
Figure 7A:
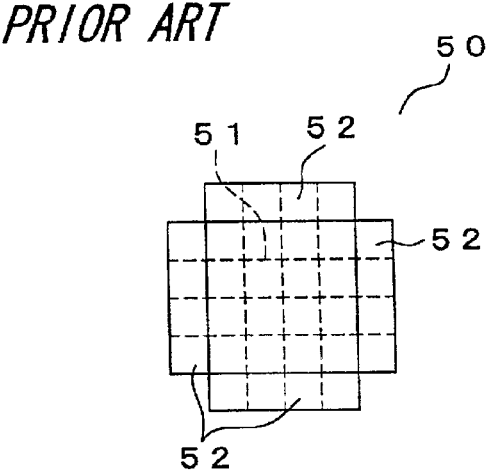
FIG. 7 is an example of a conventional process of detecting a pattern edge.
Figure 7B:
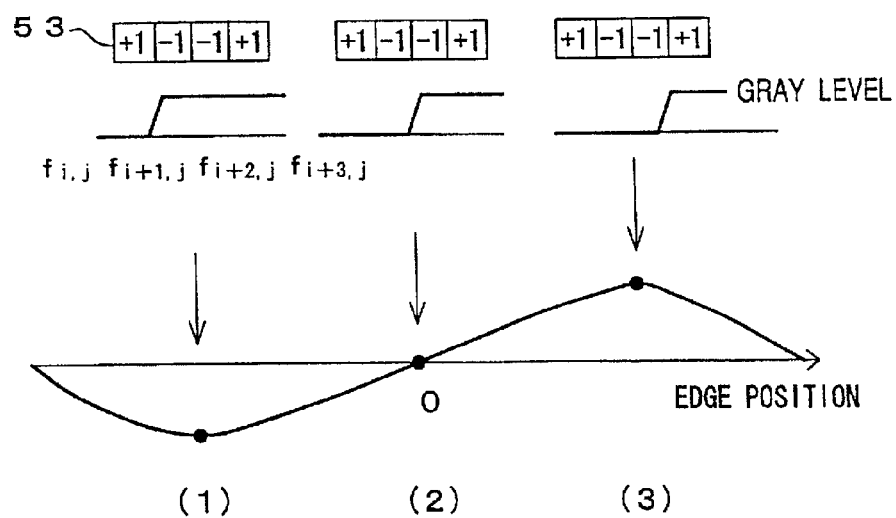

FIG. 6 is a schematic view of another defect detection system in accordance with the present invention, generally indicated at reference numeral 200. In the drawing, the elements identical to those in FIG. 1 are denoted with the same reference numerals. The defect detection system 200 has an imaging camera 6 mounted on a camera holding stage 14. The position of the camera holding stage 14 is controlled by a signal from a pattern edge position detection unit 12.

With the defect detection system 100 shown in FIG. 1, the stage 1 carrying the wafer 2 to be checked is moved to align the pattern edge with the edge of the pixels. On the other hand, the defect detection system 200 shown in FIG. 6, alignment is performed by moving either of the stage 1 or the camera holding stage 14 or both.

With the defect detection systems 100 and 200, the image of the wafer 2 to be checked is picked up by the imaging camera 6 as a gray image of 256 levels. The comparison performed in the image processing/image comparison unit 7 is 8-bit data processing.

Generally, the magnitude of background noise (noise generated at the points other than the pattern edge of a normal pattern) is approx. 10.

Therefore, when the noise at a pattern edge resulting from minute misalignment (alignment error) between the pattern edge and the edge of the pixels after the alignment is 10 or less, nearly the same level of the background noise, such an error is not recognized as a false defect.

As described above, the use of the defect detection system in accordance with the present invention can prevent the detection of misalignment between the pattern edge and the edge of the pixels as a false defect.

This allows high-precision defect detection of a pattern having a width smaller than that of one pixel of an imaging camera.

What is claimed is:

1. A defect detection system for checking any defect in a pattern to be checked by comparing the pattern with a reference pattern, including:

a stage for carrying a substrate on which a pattern to be checked is formed; an edge detection means for detecting a pattern edge of the pattern to be checked by scanning the substrate by laser beams and detecting reflected light thereof;

an imaging means positioned above the stage for picking up an image of the pattern to be checked using a charge coupled device (CCD);

a detection means for checking any defect in the pattern to be checked by comparing data of the pattern to be checked obtained by the imaging means with data of the reference pattern; and an adjustment means for adjusting a relative position of the substrate and the imaging means;

wherein the imaging means picks up an image of the pattern to be checked after the adjustment means adjusts the relative position of the substrate and the imaging means so that the pattern edge of the pattern to be checked is substantially aligned with a side of pixels of the CCD.

2. The defect detection system according to claim 1 wherein said edge detection means includes a light source of said laser beams and a detector for receiving reflected light of the laser beams.

3. The defect detection system according to claim 1 wherein said edge detection means is a means for detecting said pattern edge by radiating said substrate with two independent laser beams from two different directions.

4. The defect detection system according to claim 3 wherein horizontal components of the two laser beams are substantially orthogonal to each other.

5. The defect detection system according to claim 1 wherein said edge detection means is a means for detecting a position radiated with said laser beams at peak scattering intensity of said reflected light as a pattern edge of said pattern to be checked.

6. The defect detection system according to claim 1 wherein said edge detection means includes a polarizer selected between a linear polarizer and a phase shifter, polarizes the laser beams and radiates them on said substrate.

7. The defect detection system according to claim 1 wherein said adjustment means is a means for adjusting the relative position of said stage and said imaging means by moving at least one of said stage and said imaging means.

8. The defect detection system according to claim 1 wherein said data of the reference pattern is data of the non-defective pattern selected from a plurality of said patterns to be checked.

9. The defect detection system according to claim 1 wherein said data of the reference pattern is CAD data of said pattern to be checked.

10. The defect detection system according to claim 1 wherein a pattern width of said pattern to be checked is smaller than a width of said pixels.

* * * * *